United States Patent [19]

Watanabe et al.

[11] Patent Number: 5,175,098
[45] Date of Patent: Dec. 29, 1992

[54] EXPRESSION AND DIAGNOSTIC USE OF GAG ENCODED PEPTIDES WHICH ARE IMMUNOLOGICALLY REACTIVE WITH ANTIBODIES TO HIV

[75] Inventors: Susan M. Watanabe, Seattle; Wesley L. Cosand, Bothell; Susan McArdle; Pamela J. Ward, both of Seattle, all of Wash.

[73] Assignee: Genetic Systems Corporation, Redmond, Wash.

[21] Appl. No.: 388,308

[22] Filed: Jul. 28, 1989

Related U.S. Application Data

[63] Continuation of Ser. No. 763,460, Aug. 7, 1985, abandoned.

[51] Int. Cl.⁵ .................. C12N 15/49; C12P 15/00; C12P 21/00; C12P 21/02
[52] U.S. Cl. .................................... 435/69.3; 435/5; 435/71.2; 435/172.1; 435/172.3; 435/252.3; 435/320.1; 435/974; 536/27; 935/9; 935/12; 935/27; 935/72; 935/73; 930/220
[58] Field of Search .................. 435/69.1, 71.2, 252.3, 435/69.3, 5, 172.3, 320.1, 252.33; 536/27

[56] References Cited

PUBLICATIONS

F. Bárre-Sinoussi et al., "Isolation of a T-Lymphotropic Retro-virus from a Patient at Risk for Acquired Immune Deficiency Syndrome (AIDS)", *Science* 220:868-871, 1983.
M. Popovic et al., "Detection, Isolation, and Continuous Production of Cytopathic Retroviruses (HTLV-III) from Patients with AIDS and Pre-AIDS", *Science* 224:497-500, 1984.
J. A. Levy et al., "Isolation of Lymphocytopathic Retroviruses from San Francisco Patients with AIDS", *Science* 225:840-842, 1984.
E. Vilmer et al., "Isolation of New Lymphotropic Retroviruses from Two Siblings with Haemophilia, B, One with AIDS", *Lancet* i: 753-757, 1984.
S. Wain-Hobson et al., "Nucleotide Sequence of the AIDS Virus, LAV", *Cell* 40:9-17, 1985.
M. A. Muesing et al., "Nucleic Acid Structure and Expression of the Human AIDS?Lymphadenopathy Retrovirus", *Nature* 313:450-458, 1985.
R. Sanchez-Pescador et al., "Nucleotide Sequence and Expression of an AIDS-Associated Retrovirus (AR-V-2)", *Science* 227:484-492, 1985.
J. Schupbach et al., "Serological Analysis of a Subgroup of Human T-Lymphotropic Retroviruses (HTLV-III) Associated with AIDS", *Science* 224:503, 1984.
J. Schupbach et al., "Antibodies to HTLV-III in Swiss Patients with AIDS and Pre-AIDS and in Groups at Risk for AIDS", *New Engl. J. Med.* 312:265-270, 1985.
V. S. Kalyanaraman et al., "Antibodies to the Core Protein of Lymphadenopathy-Associated Virus (LAV) in Patients with AIDS", *Science* 225:321-323, 1984.
Crowl et al., *Cell* 41:979, 1985.
N. T. Chang et al., *Science* 228:93, 1985.
L. Ratner et al., *Nature* 313:277, 1985.
Gray, M. R. et al (1982) *Proc. Natyl. Acad. Sci. USA* 79, 6598–6602.
Hopp, T. P. et al. (1981) *Proc. Natl. Acad. Sci. USA* 78, 3824–3828.
Chou, P. Y. et al. (1978) *Ann. Rev. Biochem* 47, 251–276.
Tacon, W. et al. (1980) *Molec. Gen. Genet.* 177 427–438.

*Primary Examiner*—Richard A. Schwartz
*Assistant Examiner*—Johnny F. Railey, II
*Attorney, Agent, or Firm*—Townsend and Townsend

[57] ABSTRACT

Immunologically reactive gag proteins of LAV are expresesed in bacterial cells. The gag proteins are encoded by a recombinant plasmid containing procaryotic transcriptional and translational signals for expression, followed downstream by a DNA sequence comprising a portion of the gag region of LAV. Preferred signals for expression are selected from an inducible and/or suppressible operon, such as the trp operon. The gag proteins are isolated from the bacterial host and are utilized in diagonstic assays which detect the presence of LAV antigens or antibodies immunologically reactive with LAV. Further, the proteins produced by the method disclosed may be used as a vaccine against infection by the caustive virus for acquired immune deficiency syndrome.

25 Claims, 5 Drawing Sheets

Fig. 1

Fig. 2 pJH12: 5' GAG ATC CCC GGG GAT CCT CTA GAG TCG ACC
TGC AGC CCA AGC TT 3'
(BamHI over GAT CCT; HindIII over AGC TT)

pJH14: 5' GAG ATC CCC CCG AAT TCG GGG GGA TCC TCT
AGA GTC GAC CTG CAG CCC AAG CTT 3'
(BamHI over GGA TCC; HindIII over AAG CTT)

EXPRESSION AND DIAGNOSTIC USE OF GAG ENCODED PEPTIDES WHICH ARE IMMUNOLOGICALLY REACTIVE WITH ANTIBODIES TO HIV

This is a continuation of application Ser. No. 06/763,460, filed Aug. 7, 1985, now abandoned.

TECHNICAL FIELD

The present invention relates generally to the expression of viral proteins through the use of recombinant DNA technology, and more specifically, to the expression of proteins which are immunologically reactive with antibodies to lymphadenopathy-associated virus (LAV), now known as Human Immunodeficiency Virus (HIV).

BACKGROUND ART

Acquired immune deficiency syndrome (AIDS) is a transmissible deficiency of cellular immunity characterized by opportunistic infections and certain rare malignancies. The dominant risk groups for AIDS include homosexually active males, intravenous drug abusers, recipients of transfusions and blood products, and the heterosexual partners and children of high-risk individuals, suggesting the involvement of an infectious agent transmitted through intimate contact or blood products.

Recent evidence indicates that the infectious agent responsible for disease transmission is a novel lymphotropic retrovirus, known as lymphadenopathy-associated virus (LAV) (Barré-Sinoussi et al., *Science* 220: 868 (1983)). Similar viruses have been reported by other scientific groups (Popovic et al., *Science* 224: 497 (1984); Levy et al., *Science* 225: 840 (1984); Vilmer et al., *Lancet* 1:753 (1983)) and designated human T-cell lymphotropic virus type III (HTLV-III), AIDS-associated retrovirus (ARV), or immune deficiency-associated virus (IDAV). Still more recent data indicates that LAV, HTLV-III, ARV, and IDAV share several important characteristics, including substantial nucleotide homology (Wain-Hobson et al., *Cell* 40:9 (1985); Muesing et al., *Nature* 313: 450 (1985); Sanchez-Pescador et al., *Science* 227: 484 (1985)), and should be considered isolates of the same virus, although there is a likelihood that strain-to-strain variations among the viral isolates will exist. In addition to exhibiting substantial nucleotide homology, the isolates are similar with respect to morphology, cytopathology, requirements for optimum reverse transcriptase activity, and at least some antigenic properties (Levy, supra; Schupbach et al., *Science* 224: 503 (1984)).

As noted above, the virus is known to be transmissible through blood products (blood, blood serum, blood plasma, and fractions thereof), making it important to screen the blood products to determine if the donor has been exposed to the virus. This can be done in any of several ways, including enzyme-linked immunosorbent assay (ELISA) for the detection of antibodies to LAV and related viruses. Individuals whose blood contains antibodies to LAV are said to be "seropositive." Blood from seropositive donors may be eliminated from the blood supply upon detection, thereby helping to prevent the spread of the disease.

The immune response of individuals exposed to LAV is variable. Antibodies can be produced to any of several viral proteins, including p13, p18, p25, p36, gp43, p55, gp110, etc. (Schupbach et al., *N. Engl. J. Med.* 312: 265 (1985)). Not all individuals will make antibodies to the same proteins or to the same epitope on a given protein.

The detection of seropositive individuals, as currently practiced, has several inherent problems. Foremost among these problems is the need to isolate antigen from whole viruses for the immunological assays. This isolation requires the manipulation of large volumes of live, potentially infectious virus, and as such poses a significant safety hazard. In addition, there are concerns relating to the yield, purity, and reproducibility of virus from one preparation to another. This may result in an unacceptable number of false positives and/or negatives. Consequently, there is a need in the art for alternative methods of producing viral antigens which are useful in blood screening assays, and which further provide other related advantages.

DISCLOSURE OF INVENTION

Briefly stated, the present invention discloses DNA sequences comprising a portion of the group specific antigen (gag) region of the LAV genome, the portion coding for a protein which is immunologically reactive with antibodies to LAV. A recombinant plasmid capable of replication in bacterial host cells is also disclosed. The plasmid includes procaryotic transcriptional and translational signals for expression, followed in reading phase by the DNA sequence described above. In a preferred embodiment, signals are chosen from an operon, such as the trp operon, which is inducible and/or suppressible. Bacterial cells, such as *E. coli*, which have been transformed with the recombinant plasmid described above, are also disclosed.

Another aspect of the invention discloses a method for preparing proteins which are immunologically reactive with antibodies to LAV. The method comprises introducing into a bacterial host cell a recombinant plasmid capable of replication in bacterial host cells. The plasmid includes procaryotic transcriptional and translational signals for expression, followed in reading phase by a DNA sequence comprising a portion of the gag region of the LAV genome, the portion coding for a protein which is immunologically reactive with antibodies to LAV. Subsequent to the introduction of the plasmid, the bacterial host is grown in an appropriate medium. Expression of the protein is then induced and the protein product of the sequence is isolated from the bacterial host. The protein product may be purified subsequent to isolation, as by gel permeation chromatography.

A further aspect of the invention discloses a method for determining the presence of antibodies to LAV in a biological fluid. The method comprises incubating the biological fluid with a protein produced by bacterial cells transformed with a recombinant plasmid as described above, thereby forming a reaction mixture, and subsequently analyzing the reaction mixture to determine the presence of the antibodies. In a preferred embodiment, the step of analyzing the reaction mixture comprises contacting the reaction mixture with a labeled specific binding partner for the antibody.

Yet another aspect of the invention discloses a method for determining the presence of LAV antigen in a biological fluid, comprising incubating the biological fluid with a labeled protein produced by bacterial cells transformed with a recombinant plasmid as described above, and either sequentially or simultaneously, with an antibody to the protein such that specific binding occurs. Subsequently, the reaction mixture formed during the incubation is analyzed to determine the amount of label associated with the antibody.

A method for producing antibodies to LAV comprising immunizing an animal with a protein produced by bacterial cells transformed with a recombinant plasmid as described above, is also disclosed.

An additional aspect of the present invention discloses a method for determining the presence of antibodies to LAV in a biological fluid, comprising conjugating latex beads to a protein produced by bacterial cells transformed with a recombinant plasmid capable of replication in bacterial host cells, the plasmid including procaryotic transcriptional and translational signals for expression. The signals are followed by a DNA sequence comprising a portion of the gag region of the LAV genome, the portion coding for a protein which is immunologically reactive with antibodies to LAV. Subsequently, the biological fluid is incubated with the bead/protein conjugate, thereby forming a reaction mixture. The reaction mixture is then analyzed to determine the presence of the antibodies.

The proteins produced within the present invention, when used with a suitable carrier or diluent, form an immunologically effective vaccine composition. By administering to an individual an immunogenically effective amount of a protein encoded by a DNA sequence comprising a portion of the gag region of the LAV genome attached to a physiologically acceptable carrier, infection caused by the virus responsible for AIDS can be prevented.

Other aspects of the invention will become evident upon reference to the following detailed description and attached drawings.

BEST MODE FOR CARRYING OUT THE INVENTION

Prior to setting forth the invention, it may be helpful to an understanding thereof to set forth definitions of certain terms to be used hereinafter.

Lymphadenopathy-Associated Virus (LAV): A human T-lymphotropic retrovirus. For purposes of the present invention, a virus is considered to be the same as or equivalent to LAV if it substantially fulfills the following criteria:

(a) the virus is tropic for T-lymphocytes, especially T-helper cells (CD4+, according to the international nomenclature defined in Bernard et al., eds., *Leucocyte Typing*,New York: Springer Verlag (1984));

(b) the virus is cytopathic for infected CD4+cells (rather than transforming, as are HTLV-I and II);

(c) the virus encodes an RNA-dependent DNA polymerase (reverse transcriptase) which is $Mg^{2+}$-dependent (optimum concentration 5 mM, optimum pH 7.8, not inhibitable by actinomycin D) and can employ oligo $(dT)_{12-18}$ as a primer for reverse transcription from its 3' LTR;

(d) the virus bands in a sucrose gradient at a density of approximately 1.16;

(e) the virus can be labeled with [$^3$H] uridine;

(f) the virus is distinct by immunological and nucleotide sequence criteria from members of the HTLV-I/II family of viruses (by this criterion HTLV-III is not to be considered a member of the HTLV-I/II family);

(g) the virus is substantially cross-reactive immunologically with the proteins encoded by the gag and env regions of LAV; and (h) the virus shares substantial nucleotide homology (75-100%) and amino acid sequence homology (75-100%) with LAV.

Immunologically Reactive: An antigen and an antibody are said to be "immunologically reactive" if they are capable of binding specifically to each other, typically with an affinity of at least $10^6 M^{-1}$, more often at least $10^8 M^{-1}$.

Transformed or Transformation: The process of stably and heritably altering the genotype of a recipient cell or microorganism by the introduction of purified DNA.

Lymphadenopathy-associated virus (LAV) can be isolated from patients with AIDS or lymphadenopathy syndrome. The lymph nodes of such patients are typically biopsied and placed in culture medium supplemented as necessary to support growth. A mitogen such as interleukin-2 (IL-2) or phytohemagglutinin (PHA) can be included; antiserum to human interferon can also be included. Reverse transcriptase activity typically appears about day 15 of culture. indicating the presence of virus. The virus can be concentrated from the culture supernatant using a non-ionic detergent, followed by banding in a sucrose gradient. These and other methods of purification are well known in the art and are described, for example, in Montelaro et al., *J. Virology* 42: 1029 (1982).

LAV can be propagated in any of a number of ways. It can be cultured in T-lymphocytes derived from umbilical cord or peripheral blood or from bone marrow. Alternatively, it can be propagated in immortalized T-cells or B-cells; see, for example, Popovic et al., *Science* 224: 497 (1984), and Montagnier et al., *Science* 225: 63 (1984). Growth of the virus is usually monitored by the presence of reverse transcriptase activity.

A genomic clone of LAV can be prepared by any of several methods well known in the art, including but not limited to those described by Hahn et al., *Nature* 312: 166 (1984); Alizon et al., *Nature* 312: 757 (1984); Luciw et al., *Nature* 312: 760 (1984); and Muesing et al., *Nature* 313: 450 (1985).

Briefly, in one of these methods (Alizon et al.) DNA is isolated from LAV-infected T-cells of a healthy donor, partially digested with a restriction endonuclease such as Hind III, and the resultant digest fractionated electrophoretically. Fragments which correspond in size to the size of the entire LAV genome (approximately 9.2 Kb) are eluted from the gel, precipitated, resuspended, and ligated into the arms of an appropriately restricted vector. The ligation mix is packaged into bacteriophage particles. Bacteria are transformed with the bacteriophage, and the clones are screened in situ for LAV inserts using a suitable probe (such as cDNA made from LAV-RNA). From a positive clone, the desired region of LAV can be subcloned into a bacterial plasmid vector, such as pUC 18. Further sub-cloning can be desirable to remove unwanted sequences and to add additional restriction sites (in the form of a polylinker) at either end for the purpose of facilitating cloning into an expression vector.

The LAV sequences can then be subcloned into an inducible expression vector. A variety of expression vectors are known in the art and include λ gt 11:Tn5 (Hall et al., *Nature* 311: 379 (1984); trp E (Paul et al., *Eur. J. Cell Biol.* 31: 171 (1983); pINIII (Masui et al., *Biotechnology*, Jan. 1984, p. 81).

The resultant proteins can be partially purified and used for a variety of purposes, including, as immunogens and antigens in immunoassays. For use as immunogens, the proteins can be injected into an animal, such as a mouse, rabbit, goat, etc., either in buffered solution or in adjuvant. Alternatively, the proteins can be purified by polyacrylamide gel electrophoresis and the bands of interest excised from the gel, triturated, and resuspended in buffer for injection into the host animal. Polyclonal or monoclonal antibodies can be prepared. For use as antigens in immunoassays, the proteins can be employed in labeled or unlabeled form. Where they are labeled, the labels can include radioisotopes, fluorophores, enzymes, luminescers, or particles. These and other labels are well known in the art and are described, for example, in the following U.S. Pat. Nos. 3,766,162; 3,791,932; 3,817,837; 3,996,345; and 4,233,402.

Assays employing the recombinant proteins of the instant invention can be heterogeneous (i.e., requiring a separation step) or homogeneous. If the assay is heterogeneous, a variety of separation means can be employed, including centrifugation, filtration, chromatography, or magnetism.

One preferred assay for the screening of blood products or other physiological fluids for the presence of antibodies is an ELISA. Typically, antigen (in this case, one or a combination of recombinant proteins) is adsorbed to the surface of a microtiter well. Residual protein-binding sites on the surface are then blocked with an appropriate agent, such as bovine serum albumin (BSA), heat-inactivated normal goat serum (NGS), or BLOTTO (a buffered solution of nonfat dry milk which also contains a preservative, salts, and an antifoaming agent). The well is then incubated with a sample suspected of containing specific antibody. The sample can be applied neat, or, more often, it can be diluted, usually in a buffered solution which contains a small amount (0.1-5.0% by weight) of protein, such as BSA, NGS, or BLOTTO. After incubating for a sufficient length of time to allow specific binding to occur, the well is washed to remove unbound protein and then incubated with labeled anti-human immunoglobulin (αHuIg). The label can be chosen from a variety of enzymes, including horseradish peroxidase (HRP), β-galactosidase, alkaline phosphatase, and glucose oxidase. Sufficient time is allowed for specific binding to occur, then the well is again washed to remove unbound conjugate, and the substrate for the enzyme is added. Color is allowed to develop and the optical density of the contents of the well is determined visually or instrumentally.

For convenience, reagents for ELISA may be titer plates to which viral proteins made by recombinant techniques have been pre-adsorbed, various diluents and buffers, labeled conjugates for the detection of specifically bound antibodies, and other signal-generating reagents, such as enzyme substrates, cofactors, and chromogens.

Sera of LAV-infected individuals contain antibodies to many LAV proteins, including p13, p18, p25, p36, gp43, p55, gp110, etc. Although not all individuals make antibodies to the same proteins, individual sera are most consistently reactive with antibodies to the gag proteins, p25 and p18, and to the env proteins, gp43 and gp110. Variation between individuals may be due to several factors, including disease progression. For example, there is some evidence that antibodies to core proteins are prominent during the earliest stages of the disease, but decline with progression of immune suppression. In contrast, antibody titers to the envelope glycoproteins are thought to persist during the later stages of the disease.

Additional variation in response may be due to polymorphism in the genes encoding viral proteins. Different isolates of LAV possess significant alterations in the env protein. Interestingly, the gag protein sequences are highly conserved.

In every seropositive sample examined, antibodies to at least one of the gag proteins (p18 or p25) or one of the env proteins (gp43 or gp110) have been seen. However, none of these proteins are universally recognized by seropositive individuals. It therefore seems essential that blood be screened for antibodies to at least one gag and one env protein. In a previous patent application, U.S. Ser. No. 721,237, entitled "Expression of Immunologically Reactive Viral Proteins," the disclosed invention utilizes portions of the envelope (env) region of the LAV genome, which codes for a protein which is immunologically reactive with antibodies to LAV. The present invention utilizes portions of the gag region of the LAV genome, which codes for a protein which is also immunologically reactive with antibodies to LAV. In combination, proteins encoded by the gag and env regions can be utilized to detect seropositive individuals with a high degree of sensitivity.

Another application of the recombinant proteins of this invention is as vaccines for human use. The recombinant proteins can be extensively purified and formulated in a convenient manner, generally in concentrations of 1 ug to 20 mg per kg of host. Physiologically acceptable carriers, such as sterile water, saline, buffered saline, etc., can be employed. Adjuvants, such as aluminum hydroxide, can also be employed. The vaccine can be administered by intravenous, subcutaneous, intramuscular, or peritoneal injection. One injection can be sufficient, but more often, multiple injections at weekly to monthly intervals are preferred.

Alternatively, vaccinia virus recombinants can be constructed which express regions of the LAV genome. For example, the constructs of this invention can be inserted into a plasmid such as pMM34 (Mackett et al., *Science* 227: 433, 1985) and vaccinia virus hybrids containing the resultant chimeric plasmid, formed by homologous recombination. Immunization with such recombinant virus vaccines has been shown to be effective in eliciting protective immunity in animals to hepatitis B virus and vesicular stomatitis virus (Smith et al., *Nature* 311: 578, 1984).

The use of a recombinant protein vaccine in this manner eliminates the need to compose vaccines from inactivated preparations or a virulent strains of pathogenic microorganisms.

In the following example, two overlapping regions of LAV-gag were selected for expression (FIG. 3). The choice was influenced by the finding that p18 and p25 were the gag proteins most reproducibly reactive with sera from LAV-infected individuals. Our selection within these sequences was dictated by the location of hydrophilic regions and protease cleavage sites (both of which may be exposed at the surface of the protein and immunogenic) as well as by the size limitation for efficient expression in the chosen vectors (trp E).

The LAV genomic clone designated λ J19 was subcloned into the bacterial plasmid vector, pUC 18. The resultant subclone, designated pBT-1, was further subcloned to yield pSS-5 and pBS-5, which contained predominantly gag and pol sequences. The gag sequences were further subcloned into pIC19R, (forming plasmids pSM002 and pBPB14), and then regions of the gag sequence were transferred into the trp E inducible expression vector. The gag DNA was inserted in-frame downstream of the trp E gene, resulting in the expression of a trp E-gag fusion protein when $E.$ $coli$ were transformed with this construct. The resultant proteins were partially purified and characterized by their reactivity in ELISA with sera from known seropositive and known seronegative individuals. Two useful constructions, designated pGAG-2 and pGAG-3, were identified.

The following example is offered by way of illustration, and not by way of limitation.

EXAMPLE

A. Construction of the trp-gag expression vectors

Any of several bacterial expression systems can be used to express foreign proteins. The trp E system was chosen for the expression of LAV-gag sequences because it contains a strong inducible promoter, but its expression can also be suppressed so that foreign (and potentially toxic) protein does not accumulate within the bacteria for long periods of time.

Figure 4:
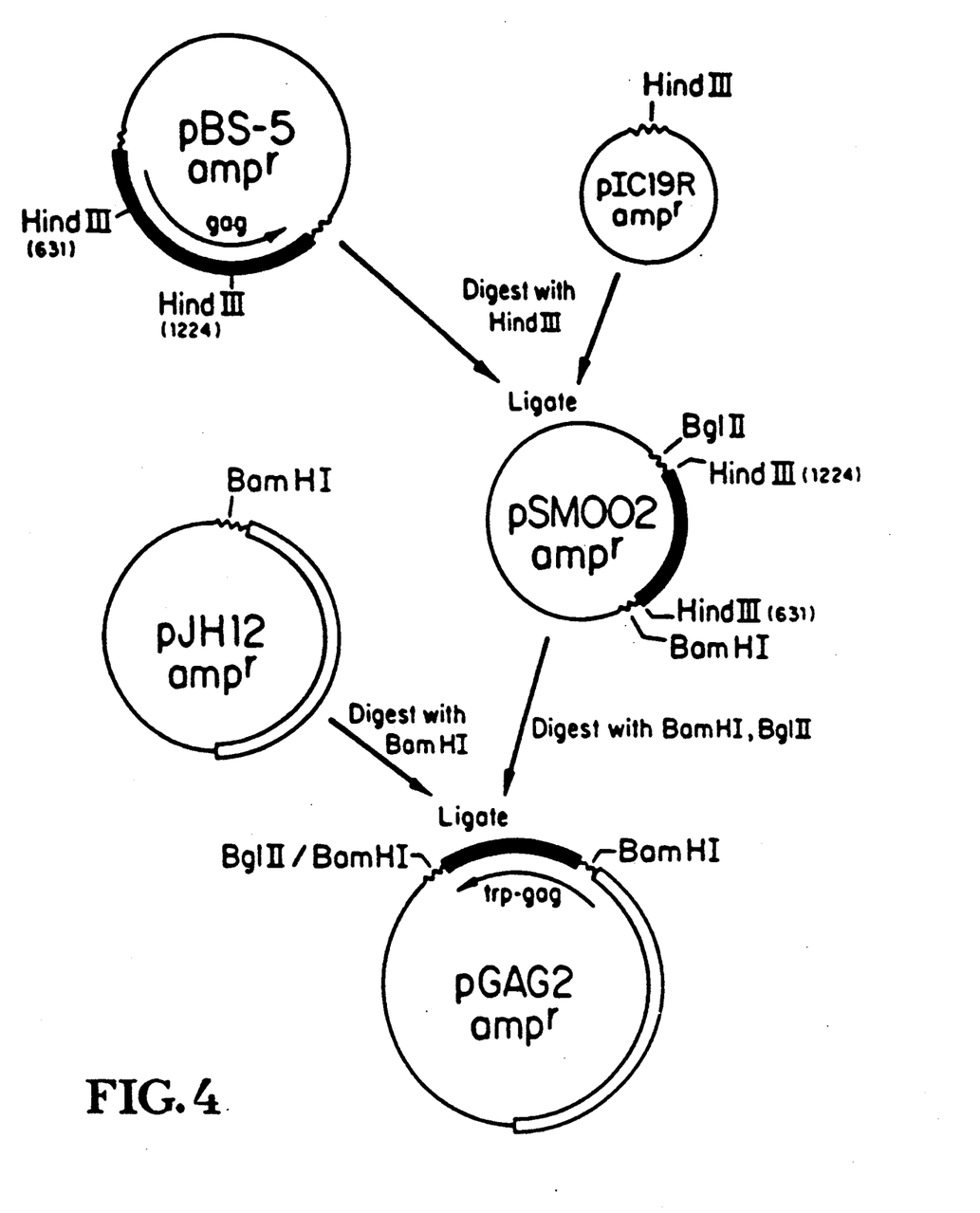
FIG. 4 illustrates the construction of pGAG-2 from pJH 12 and pSM002.

Expression vectors are limited by the type and reading frame of their restriction sites. (or example, the trp E expression vectors require that the DNA insert possess Bam HI, Hind III, or EcoRI restriction site compatible termini. More diversity can be introduced by first subcloning the region of interest into an intermediate vector which possesses a broader range and altered arrangement of restriction sites. The region of interest can then be introduced into an expression vector by using restriction sites provided by the intermediate vector.

Our strategy, therefore, was to first subclone most of the gag region of the LAV genome into a transfer vector, pIC19R. Then, various fragments of these subclones were ligated into either of two trp expression vectors (pJH 12, pJH 14), which differed only in the reading frame of the restriction sites in the polylinker region (see FIG. 2).

1. Subcloning LAV genome a. Preparation of phage DNA

The entire LAV genome was obtained from the Pasteur Institut in the form of λ phage particles containing a 9.2 Kb genomic DNA insert in the Hind III site of phage λ L47.1. This clone is referred to as λ J19 and is described in Wain-Hobson et al., *Cell* 40: 9 (1985). λ J19 phage particles were transfected into the Q359 strain of *E. coli* K-12 (the genotype of Q359 is hsdRk−, hsdMk+, supF, φ80, P2) according to the procedure of Maniatis et al., *Molecular Cloning: A Laboratory Manual,* New York: Cold Spring Harbor Laboratory, 1982, at p. 64. A single plaque was picked and the phage amplified by the plate lysate method (Maniatis, supra, at p. 65). After a nine-hour incubation at 37° C., the plates (100 mm diameter) containing confluent plaques were overlaid with 5 ml of 100 mM NaCl/20 mM $MgSO_4$/50 mM Tris, pH 7.5. After incubating for twelve hours at 4° C., the liquid was collected and extracted two times with an equal volume of chloroform.

To 10 ml of the resultant aqueous phase containing phage particles was added 2 ml 0.25 M EDTA/2.5% SDS/0.5 M Tris, pH 9, and the suspension was incubated at 70° C. for fifteen minutes to disrupt the phage. 2.5 ml 8 M potassium acetate was added, and the solution was incubated on ice for fifteen minutes, then centrifuged for ten minutes at 12,000 xg at 4° C. to pellet protein. The supernatant was transferred to a 50 ml polypropylene centrifuge tube and extracted with an equal volume of phenol (pH 8, equilibrated with 1 M Tris, pH 8) at 20° C. The aqueous phase was then extracted with an equal volume of chloroform:isoamyl alcohol (24:1) at 20° C. To the aqueous phase was then added 2.5 volumes of 95% ethanol to precipitate the DNA. After centrifugation, the DNA pellet was dried and resuspended in 10 mM Tris HCl, pH 7.4/1 mM EDTA.

b. Subcloning the gag region

Approximately 12 ug of λ J19 DNA prepared in A.1.a above was digested to completion with the restriction enzyme Sst I (Bethesda Research Labs, Bethesda, MD), which only cuts in the LTR regions of this isolate of LAV. The digest mixture was electrophoresed at 1 V/cm through 0.9% agarose in 0.089 M Tris-borate/0.089 M boric acid/1 mM EDTA. The position of the 9.1 Kb fragment was determined relative to molecular weight standards after staining with ethidium bromide. This band was electroeluted into NA45 paper (Schleicher and Schuell, Keene, NH). The DNA was recovered from the paper according to instructions provided by the manufacturer.

The 9.1 Kb Sst I fragment was ligated into the Sst I digested vector pUC 18, at a ratio of 10 insert molecules: 1 vector molecule. *E. coli* strain HB101 was transformed with the ligation mix by the $CaCl_2$ procedure of Maniatis et al. (supra) and plated onto LB plus ampicillin (200 ug/ml) agar plates.

Single colonies were picked and diluted into 3 ml LB plus ampicillin medium and grown overnight at 37° C. with constant shaking. Plasmid DNA was prepared by the alkaline lysis method (Maniatis et al., supra, at p. 368). One colony was selected which contained the 9.1 Kb Sst I insert in an orientation such that the Eco RI site in the polylinker was closest to the 5′ end of the LAV genome, as determined by restriction analysis of the plasmid DNA. This subclone was designated pBT-1 (ATCC Accession #53069) (FIG. 1).

Two subclones were made from plasmid pBT-1 (see FIG. 1). For the first (pSS-5), pBT-1 was digested with Sal I and then religated. For the second, pBS-5, pBT-1 was digested with Bam HI and BglII and then religated. In each case, the 5′ part of the LAV genome was retained with the vector. HB101 cells were transformed with the ligated DNA and colonies containing the pSS-5 and pBS-5 inserts were identified by restriction analysis of the purified plasmid DNA.

Regions of pSS-5 and pBS-5 were then subcloned into the intermediate vector, pIC19R. As discussed above, this provided the necessary restriction sites in the correct reading frame for transfer to the expression vectors.

Specifically, the Hind III fragment of pBS-5 (bp 631 to bp 1258 of the LAV genome; numbering according to Wain-Hobson et al., Cell 40: 9 (1985)) was ligated into Hind III and calf intestinal phosphatase treated pIC19R (FIG. 4). The ligated DNA was taken up by CaCl₂-shocked E. coli TB-1. Using the chromagenic substrate 5-bromo-4-chloro-3-indodlyl-βgalactosidase (Sigma), ampicillin resistant colonies were screened for inactivation of β-galactosidase due to insertion of the gag sequence. The orientation of the insert was determined by digesting plasmid DNA with Pvu II. The resultant plasmid is referred to as pSM002.

Figure 5:
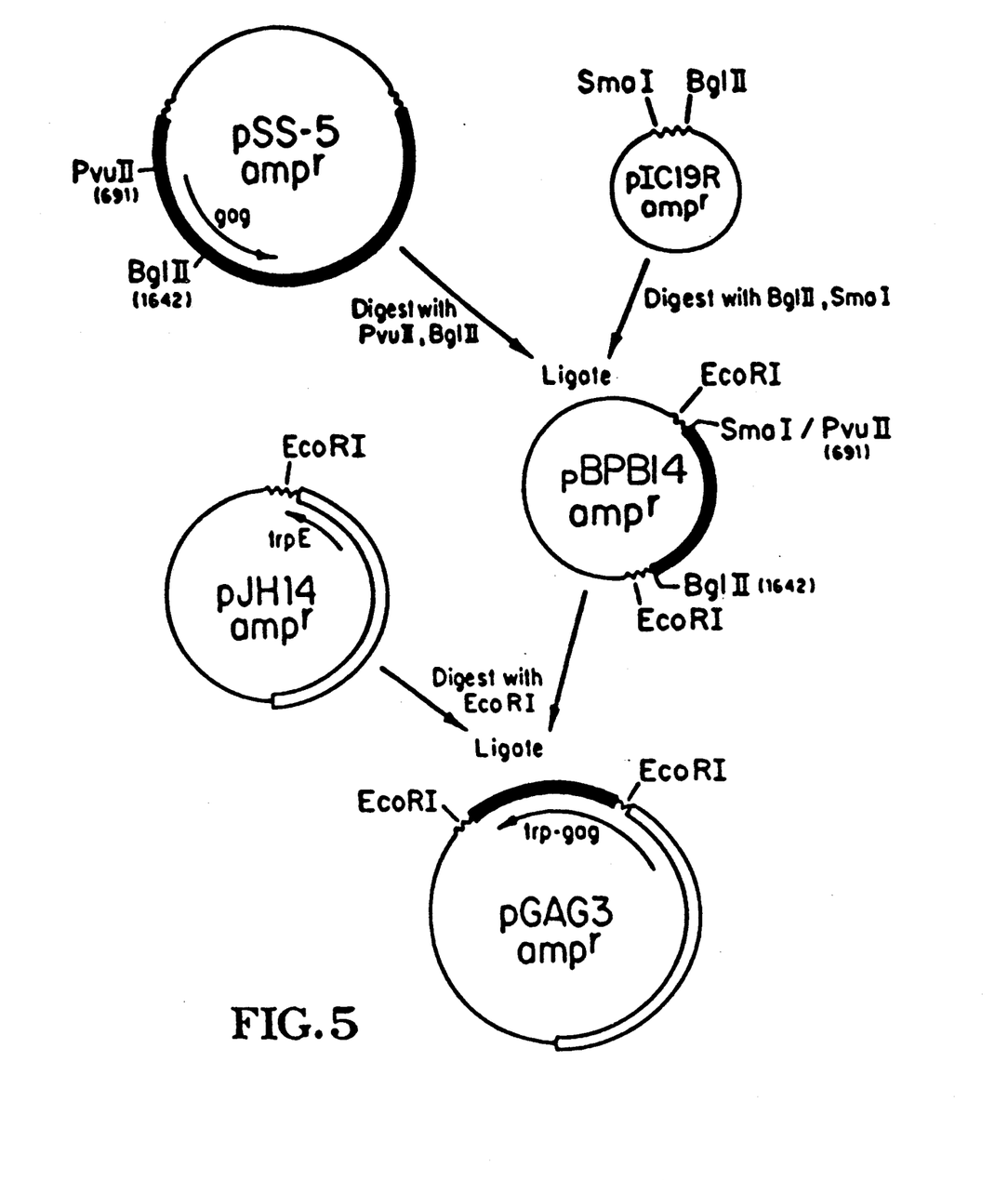
FIG. 5 illustrates the construction of pGAG-3 from pJH 14 and pBPB14.

The Pvu II-Bgl II fragment (bp 691 to bp 1642 of the LAV genome) was ligated into Sma I and Bgl II digested pIC19R (FIG. 5). The ligated DNA was taken up by E. coli HB101 and the resultant ampicillin resistant colonies screened with the chromogen as described above. Candidate colonies were further screened by restriction analysis of plasmid DNA. The resultant plasmid is referred to as pBPB14.

2. Insertion of the gag sequence into trp vectors

Figure 1:
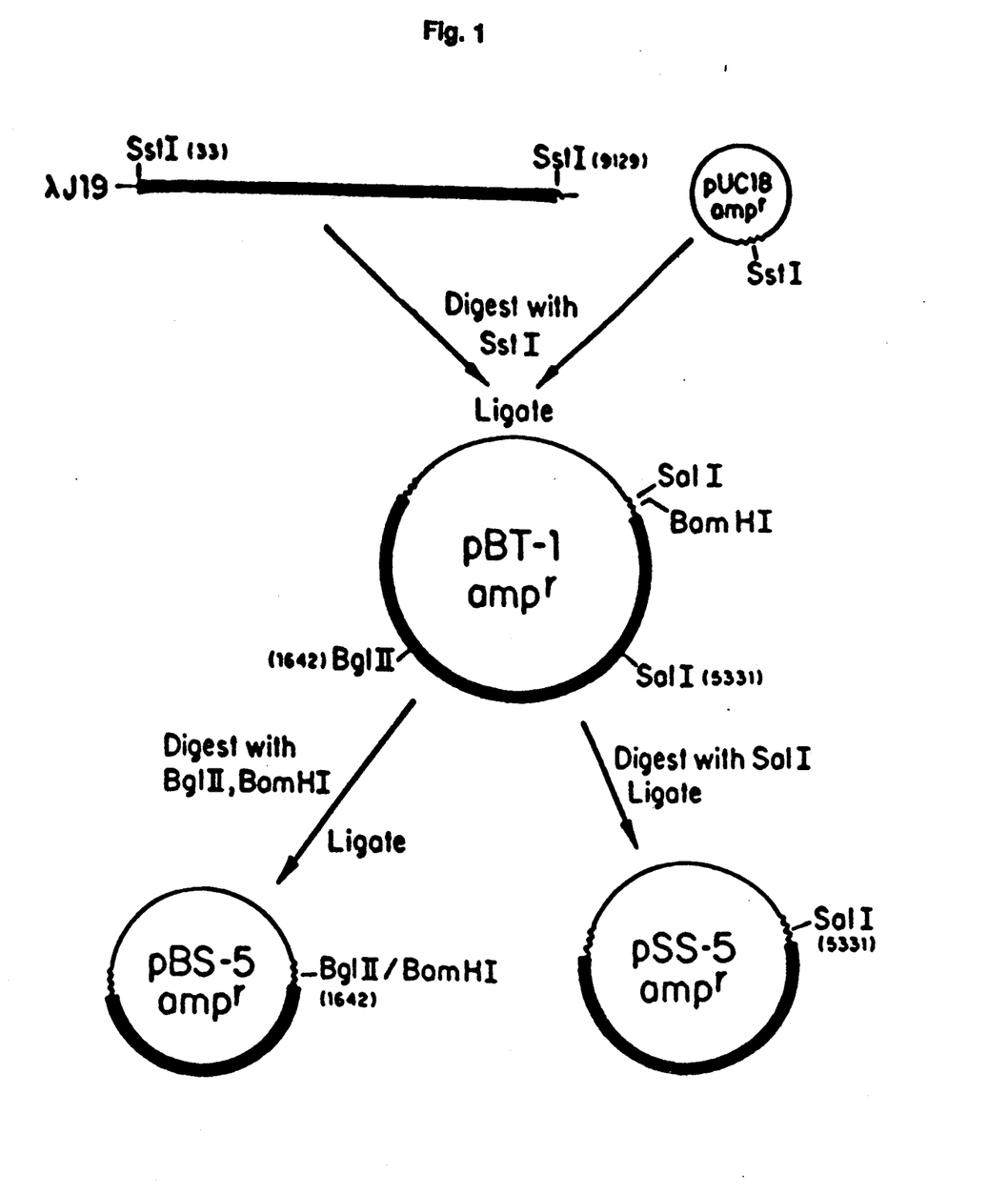
FIG. 1 illustrates the construction of pSS-5 and pBS-5 from λJ19.
Figure 2:
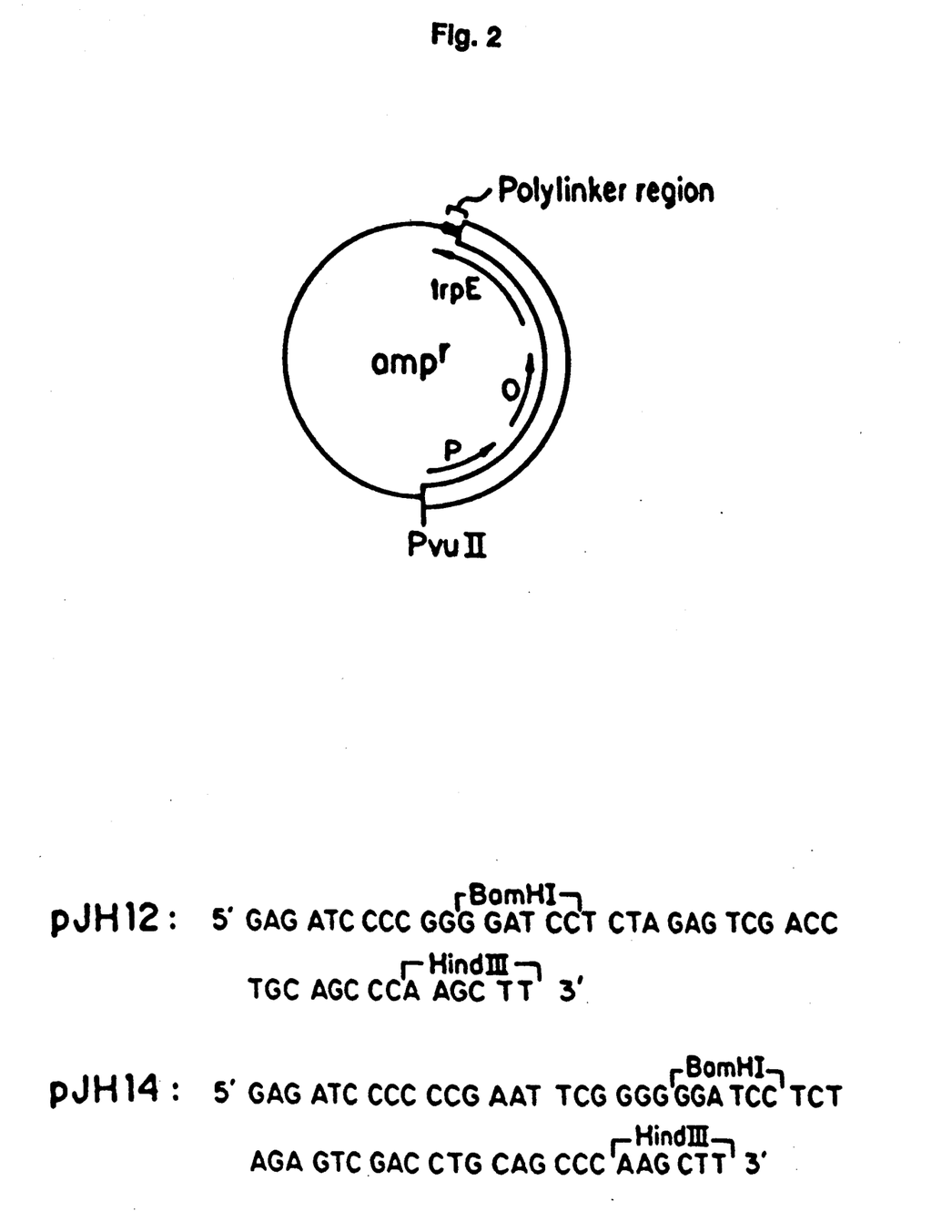
FIG. 2 illustrates the trp E expression vectors pJH 12 and pJH 14, including the polylinker sequences.
Figure 3:
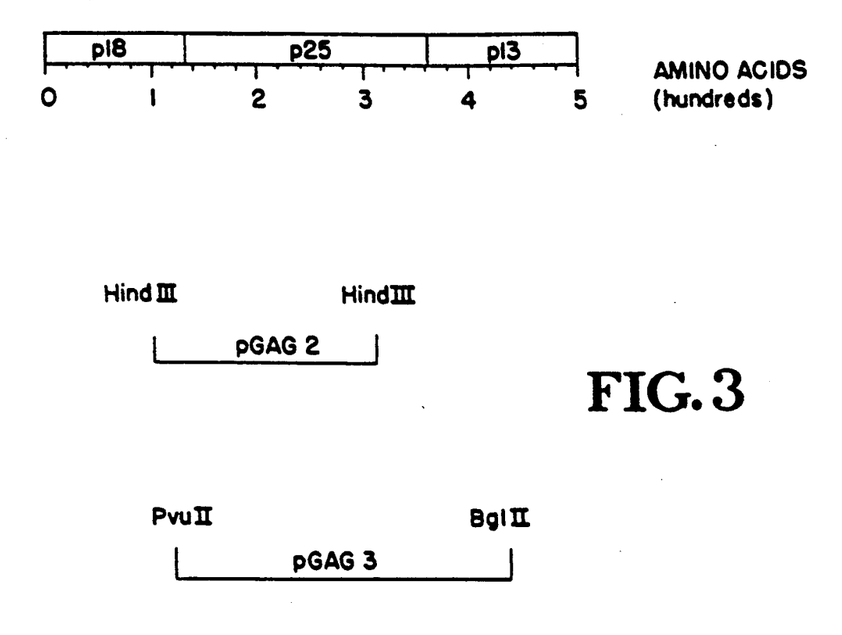
FIG. 3 illustrates the origin of the LAV inserts in pGAG-2 and pGAG-3.

The expression vectors contained the E. coli trp operon promotor, operator, and trp E gene inserted into pBR322 (FIG. 2). The trp E gene was truncated at its 5'-most Bgl II site by the insertion of a polylinker sequence (Konopka et al., J. Virol. 51: 223 (1984)). The different trp vectors (pJH 12 and pJH 14) differed according to the reading frame of the restriction sites within the polylinker region. Insertion of an open reading frame into the appropriate vector results in the production of a fusion protein with trp E sequences at the amino terminal end (Spindler et al., J. Virol. 49: 132 (1984)).

pGAG-2 (ATCC Accession #53111) was constructed by digesting the Hind III gag subclone (pSM002, FIG. 4) with Bgl II and Bam Hl. Bgl II and Bam Hl sites were located within the bracketing polylinker region of pIC19R. The gag fragment was gel purified and ligated into Bam Hl digested pJH12 (FIG. 4). Ligated DNA was taken up by CaCl₂-shocked E. coli HB101 and colonies were grown in the presence of ampicillin (100 ug/ml) and tryptophan (40 ug/ml). Tryptophan was used to suppress expression of the foreign protein, accumulation of which may be deleterious to the bacteria. Candidate ampicillin resistant colonies were identified by hybridization with a radioactively labeled gag DNA probe. Restriction analysis of minilysates was used to confirm the presence and orientation of the insert.

pGAG-3 (ATCC Accession #53112) was constructed by EcoRl digestion of pBPB14, which contains the gag region between Pvu II (bp 691) and Bgl II (bp 1642), as shown in FIG. 5. The EcoRl sites are in the polylinker sequences bracketing the gag sequences. The gag fragment was gel purified and ligated into EcoRl and calf intestinal phosphatase treated pJH14. E. coli HB101 cells were transformed with the ligated DNA, plated as described above, and screened by restriction analysis to confirm the presence and orientation of the gag sequence within pJH14.

Escherichia coli transformants containings pGAG-2 have been deposited as ATCC Deposit No. 53111 and Escherichia coli transformants containing pGAG-3 have been deposited as ATCC Deposit No. 53112 at The American Type Culture Collection, 12301 Parklawn Drive, Rockville, Md. 20852 on May 2, 1985.

B. Protein expression

1. Transformation of E. coli with the trp-gag constructs

Each of the recombinant trp-gag expression plasmids was transferred from E. coli HB101 into E. coli C600, because the latter is a better host for protein production. Transfer involved transformation of CaCl₂-shocked C600 with supercoiled DNA from minilysates of HB101. Bacteria were plated in the presence of ampicillin and tryptophan as described (Konopka et al., J. Virol. 51: 223 (1984)). Drug-resistant colonies were screened by minilysates to confirm the presence of the appropriate plasmid.

2. Expression of trp-gag proteins

Growth and induction of E. coli C600 transformed by the trp expression vectors were as described (Spindler et al., J. Virol. 49: 132 (1984); Konopka et al., J. Virol. 51: 223 (1984)). Briefly, minimal medium containing tryptophan (40 ug/ml) and ampicillin (100 ug/ml) was inoculated with transformed bacteria from glycerol stocks. Cultures were grown with aeration at 37° C. overnight. The overnight cultures were then inoculated at 1:100 into fresh minimal medium containing ampicillin (100 ug/ml) but no tryptophan. These cultures were grown with aeration for 2-3 hours (up to early log phase) at 37° C. The inducer, 3-β-indoleacrylic acid (Sigma), was added to a final concentration of 20 ug/ml from freshly made stocks at 20 mg/ml in 95% ethanol.

Induced cultures were grown at 37° C with aeration for 4 to 5 hours and then pelleted and, optionally, frozen. Protein yields from pGAG-2 and pGAG-3 were typically between 10-30 mg/liter.

C. Isolation and purification of trp-gag proteins

Fusion proteins were partially purified from cell pellets as described (Konopka et al., J. Virol. 51: 223 (1984)). Briefly, bacteria were resuspended in 100 ml of 50 mM Tris, pH 7.5/0.5 mM EDTA/150 mM NaCl (TNE) per liter of induced culture. Lysozyme (Sigma) was added to a final concentration of 1 mg/ml. After fifteen minutes at 0° C, NP40 was added to the mixture to a final concentration of between 0.05% and 0.2% for ten minutes at 0° C. 1-2 mg of DNase (Sigma) was then added with 150 ml of DNase buffer (1.5 M NaCl/12 mM MgCl₂). Reaction mixtures were incubated until they were no longer viscous, usually several hours to overnight. Insoluble proteins were then pelleted by centrifugation for 15 minutes at 8000 xg at 0° C. Pellets were washed two times in TNE and then analyzed for the presence of insoluble proteins by denaturing polyacrylamide gel electrophoresis. Proteins were visualized by staining with Coomassie brilliant blue.

Alternatively, the insoluble pellet was denatured and reduced by resuspending the pellet from about 200 ml of cells in 180 ul of 0.14 M Tris HCl, pH 7.8/6% SDS and 20 ul of β-mercaptoethanol and heating at 95° C.-100° C. for 20 minutes. The sample was then dried in a Speed Vac Concentrator (Savant Instruments, Hicksville, NY). In order to remove the SDS, the sample was extracted as follows: the pellet was resuspended in 1 ml of acetone/triethylamine/acetic acid/water (17/1/1/1) and vigorously vortexed, the suspension was chilled on ice for one hour, centrifuged and the supernatant discarded. This extraction was repeated twice with 0.4 ml of the above acetone mixture, and then twice with 0.4 ml of acetone alone. The pellet was then dried in the Speed Vac Concentrator.

The protein pellet was then dissolved in 1.4 ml of 6M guanidine hydrochloride/0.1 M Tris HCl, pH 8.5/10 mM DTT and incubated at 37° C. for 4 hours. Any particulate material was removed by centrifugation. The sample, contained in the supernatant, was loaded onto a 1.6×96 cm Sephacryl S-300 column (Pharmacia, Piscataway, N.J.) equilibrated in 6 M guanidine hydrochloride/10 mM EDTA/1 mM DTT. The column was eluted with the same buffer and the absorbance of the eluted material was measured at 280 nm.

The fractions were assayed by ELISA with LAV seropositive sera and with E. coli seropositive sera, to determine specific and contaminating reactivities, respectively. The fractions showing reactivity with the former but not with the latter serum were used in subsequent ELISA of patient sera.

D. Immunological reactivity of trp-gag proteins

1. Analysis by Western blots

Aliquots from the insoluble protein preparations expressed by pGAG-2 and pGAG-3 were solubilized in 2% sodium dodecylsulfate/100 mM Tris, pH 6.8/20% glycerol/1.5 M β-mercaptoethanol and electrophoresed on denaturing polyacrylamide gels. Proteins were electrotransferred onto nitrocellulose (BA85, Schleicher and Schuell, Keene, N.H.) and the filters blocked with 5% bovine serum albumin (Sigma). Filters were then probed with E. coli-adsorbed human sera pooled from AIDS patients. The filters were developed with HRP-conjugated goat α HuIg. The pool was reactive with both trp-gag fusion proteins but not with trp E protein alone.

2. Analysis by ELISA

Column-purified GAG-2 and GAG-3 proteins were diluted in 0.05 M carbonate/bicarbonate buffer (pH 9.6) to a final concentration of 0.3 ug/ml and 3.4 ug/ml, respectively. Fifty ul aliquots were loaded per microtiter well and incubated at 4° C. overnight. Plates were then blocked with BLOTTO (5% [w/v] nonfat dry milk/0.01% thimerosol/0.01% antifoam A in 0.01 M sodium phosphate, pH 7.2/0.15 M sodium chloride) for one hour at room temperature. Sera were diluted 1:100 with a 1:1 mixture of BLOTTO and PBS (0.01 M sodium phosphate, pH 7.3/0.15 M NaCl), and 50 ul of diluted sera was added per well for one hour at 37° C. The sera were removed, and the plates were washed three times in wash buffer (0.15 M NaCl/0.05% [w/v]Tween 20) before adding 100 ul of the goat anti-human IgG/horseradish peroxidase conjugate (50% stock diluted 1:10,000 in 50 mM NaCitrate/0.05% Tween 20/1% heat-inactivated normal goat serum; obtained from Antibodies, Inc., Davis, Calif.) for one hour at 37° C. The conjugate was removed and the plates washed three times with 0.15 M NaCl/0.05% (w/v) Tween 20. The ELISA was developed by adding 100 ul/well of substrate solution (10 mg 3,3′, 5,5′-tetramethylbenzidine in 50 ml 0.05 M sodium citrate, pH 7.0) for 30 minutes at room temperature. Reactions were stopped with 100 ul/well of 3N $H_2SO_4$, and the optical density at 450 nm determined by an automated ELISA reader. Proteins produced by pGAG-2 and pGAG-3 were both found to be reactive with a panel of known seropositive sera.

The panel included sera from two healthy heterosexuals, five individuals diagnosed as LAS (lymphadenopathy syndrome) and/or homosexual, one individual with AIDS, and a pool of sera from AIDS patients. The two heterosexual sera scored negative in a whole virus ELISA. All sera from AIDS, LAS and/or homosexual individuals were confirmed as seropositive in a whole virus ELISA and by radiolabeled immunoprecipitation of LAV antigens. The results from these sera are shown in Table I. These findings demonstrate that sera reactive to LAV antigens are also reactive to our bacterially expressed gag proteins.

3. Fluorescence slide test for detection of serum antibody to LAV

Soluble protein produced as described above is conjugated to latex beads, and the protein/bead preparation is ethanol fixed onto microscope slides. An aliquot of patient serum is incubated with the protein/beads on a slide. The slides are washed, and FITC-labeled anti-human immunoglobulin in Evans blue counterstain is added. The slides are washed, and mounting medium and coverslip applied to each.

Alternatively, the protein/bead preparation is placed in test tubes for incubation with patient serum. The tubes are centrifuged and washed, and the FITC-labeled anti-human immunoglobulin in Evans blue counterstain is added. The tubes are centrifuged and the supernatant aspirated. An aliquot of the beads is placed on a microscope slide and ethanol fixed, and coverslips are mounted.

All slides are examined by fluorescence microscopy. If test serum is antibody positive, beads appear as fluorescent green spheres; if test serum is antibody negative, beads appear as red spheres.

TABLE I

Comparison of GAG-2 and GAG-3 with a Whole Virus Lysate in an ELISA for the Detection of Antibodies to LAV

| Serum No. | Diagnosis | Whole Virus Lysate | GAG-2 | GAG-3 | Confirmed as Seropos. |
|---|---|---|---|---|---|
| Y1/CDC | positive control pool | 2.000 | 1.292 | 1.580 | yes |
| 124 | LAS and/or homosexual | 1.189 | 0.762 | 0.396 | yes |
| 127 | LAS and/or homosexual | 1.046 | 0.291 | 1.093 | yes |
| 130 | LAS and/or homosexual | 0.912 | 0.420 | 1.200 | yes |
| 153 | LAS and/or homosexual | 2.000 | 1.137 | 1.073 | yes |
| 501 | AIDS | 1.109 | 1.049 | 1.556 | yes |
| 666 | unknown | 2.000 | n.d. | 1.747 | yes |
| 637 | healthy heterosexual | 0.097 | 0.113 | 0.116 | not seropositive |
| 641 | healthy heterosexual | 0.199 | 0.116 | 0.069 | not seropositive |

4. Reactivity of combination trp-gag and trp-env proteins

A trp-gag protein was combined with a trp-env protein in a microtiter well. The ELISA was then performed as describe above for GAG-2 or GAG-3 alone. Table II shows that the combination of GAG-3 and ENV-3 has a higher sensitivity for detecting seropositive individuals than for either protein alone. Of the seropositive samples, 7/7 were detected when the proteins were combined, whereas 6/7 were detected with GAG-3 or ENV-3 alone.

TABLE II

Comparison of Combined GAG-3 and ENV-3 with GAG-3 or ENV-3 Alone or for the Detection of Antibodies to LAV

| Serum No. | Diagnosis | Whole Virus Lysate | GAG-3 100 ng / ENV-3 0 | 0 / 100 ng | 100 ng / 70 ng | 50 ng / 70 ng | Confirmed as LAV Seropos. |
|---|---|---|---|---|---|---|---|
| 591 | AIDS | 1.109 | 1.663 | 2.039 | 2.271 | 1.696 | yes |
| 7 | LAS and/or homosexual | 2.0 | 0.394 | 0.498 | 0.742 | 0.627 | yes |
| 153 | LAS and/or homosexual | 2.0 | 0.542 | 2.192 | 2.178 | 2.167 | yes |
| 154 | LAS and/or homosexual | 1.069 | 0.497 | 2.054 | 2.167 | 2.007 | yes |
| 1296 | blood donor | 2.000 | 0.278 | 0.383 | 0.545 | 0.471 | yes |
| 1642 | LAS and/or homosexual | 0.998 | 0.109 | 1.529 | 1.776 | 1.768 | n.d. |
| 1709 | healthy heterosexual | 0.133 | 0.071 | 0.164 | 0.152 | 0.155 | n.d. |
| 1890 | healthy heterosexual | n.d. | 0.214 | 0.175 | 0.286 | 0.269 | not seropos. |
| 1891 | healthy heterosexual | n.d. | 0.154 | 0.155 | 0.299 | 0.279 | not seropos. |
| 923 | blood donor | 0.119 | 0.178 | 0.476 | 0.337 | 0.325 | n.d. | n.d. = Not determined.

From the foregoing, it will be appreciated that, although specific embodiments of the invention have been described herein for purposes of illustration, various modifications may be made without deviating from the spirit and scope of the invention. Accordingly, the invention is not to be limited except as by the appended claims.

We claim:

1. An isolated and purified DNA sequence comprising a portion of the gag region of the LAV genome, said portion corresponding to that from bp631 to bp1258 or from bp691 to bp1642 of LAV and coding for a protein which comprises a fragment of at least one virally encoded gag protein and which protein fragment is immunologically reactive with antibodies to LAV.

2. The isolated and purified DNA sequence of claim 1 wherein said sequence is pGAG-2.

3. The isolated and purified DNA sequence of claim 1 wherein said sequence is pGAG-3.

4. An isolated and purified DNA sequence comprising a portion of the gag region of the LAV genome, wherein said portion corresponds to bp631 to bp1258, said portion coding for a fragment of a gag protein which is immunologically reactive with antibodies to LAV.

5. An isolated and purified DNA sequence comprising a portion of the gag region of the LAV genome, wherein said portion corresponds to bp691 to bp1642, said portion coding for a fragment of a gag protein which is immunologically reactive with antibodies to LAV.

6. A recombinant plasmid capable of stable replication and expression in bacterial host cells, said plasmid including procaryotic transcriptional and translational signal for said expression, followed in reading phase by a DNA sequence comprising a portion of the gag region of the LAV genome corresponding to bp631 to bp1258 or bp691 to bp1642, said portion coding for a protein which comprises a fragment of at least one virally encoded gag protein and which protein fragment is immunologically reactive with antibodies to LAV.

7. The recombinant plasmid of claim 6 wherein said expression is inducible.

8. The recombinant plasmid of claim 7 wherein said signals are derived from the trp operon.

9. A bacterial cell stably transformed with a recombinant plasmid capable of replication and expression in bacterial host cells, said plasmid including procaryotic transcriptional and translational signals for said expression, followed in reading phase by a DNA sequence comprising a portion of the gag region of the LAV genome corresponding to bp631 to bp1258 or bp691 to bp1642 and coding for a protein which comprises a fragment of at least one virally encoded gag protein and which protein fragment is immunologically reactive with antibodies to LAV.

10. The transformed cell of claim 9 wherein said bacterial cell is *E. coli.*

11. The transformed cell of claim 9 wherein said expression is inducible.

12. The transformed cell of claim 11 wherein said signals are derived from the trp operon.

13. A method for preparing proteins which are immunologically reactive with antibodies to LAV, comprising:
    introducing into a bacterial host cell a recombinant plasmid capable of stable replication and expression in bacterial host cells, said plasmid including procaryotic transcriptional and translational signals for said expression, followed in reading phase by a DNA sequence comprising a portion of the gag region of the LAV genome which corresponds to bp631 to bp1258 or to bp691 to bp1642, said portion coding for a protein which comprises a fragment of at least one virally encoded gag protein and which protein fragment is immunologically reactive with antibodies to LAV;
    growing said bacterial host in an appropriate medium for said expression; and
    isolating the protein product of said sequence from said bacterial host.

14. The method of claim 13, including, after isolation of said protein product, purifying said product by gel permeation chromatography.

15. The method of claim 13 wherein the expression of said protein is induced by 3-$\beta$-indoleacrylic acid.

16. The method of claim 13 wherein said expression is inducible.

17. The method of claim 16 wherein said signals are derived from the trp operon.

18. A method for preparing proteins which are immunologically reactive with antibodies to LAV, comprising:

introducing into a procaryotic cell a recombinant vector capable of stable replication and expression in said procaryotic cells, said vector including transcriptional and translational signals for said expression, followed in reading phase by a DNA sequence comprising a portion of the gag region of the LAV genome, which portion corresponds to bp631 to bp1258 and codes for a fragment of a gag protein which is immunologically reactive with antibodies to LAV;

growing said procaryotic cell in an appropriate medium for said expression; and isolating the protein product of said sequence from said procaryotic cell.

19. The method of claim 18, including, after isolation of said protein product, purifying said product by gel permeation chromatography.

20. The method of claim 18, wherein the procaryotic cell is bacterial and the recombinant vector is a plasmid.

21. The method of claim 20, wherein said expression is inducible and/or suppressible.

22. A method for preparing proteins which are immunologically reactive with antibodies to LAV, comprising:

introducing into a procaryotic cell a recombinant vector capable of stable replication and expression in said procaryotic cells, said vector including transcriptional and translational signals for said expression, followed in reading phase by a DNA sequence comprising a portion of the gag region of the LAV genome, which portion corresponds to bp691 to bp1642 and codes for a fragment of a gag protein which is immunologically reactive with antibodies to LAV;

growing said procaryotic cell in an appropriate medium for said expression; and isolating the protein product of said sequence from said procaryotic cell.

23. The method of claim 22, including, after isolation of said protein product, purifying said product by gel permeation chromatography.

24. The method of claim 22, wherein the procaryotic cell is bacterial and the recombinant vector is a plasmid.

25. The method of claim 24, wherein said expression is inducible and/or suppressible.

* * * * *